(12) United States Patent
Keller

(10) Patent No.: US 8,303,661 B2
(45) Date of Patent: Nov. 6, 2012

(54) SYSTEM FOR INTERVERTEBRAL DISK PROSTHESES

(75) Inventor: Arnold Keller, Kayhude (DE)

(73) Assignee: DePuy Spine, Inc., Raynham, MA (US)

(*) Notice: Subject to any disclaimer, the term of this patent is extended or adjusted under 35 U.S.C. 154(b) by 1166 days.

(21) Appl. No.: 11/936,510

(22) Filed: Nov. 7, 2007

(65) Prior Publication Data
US 2009/0228108 A1   Sep. 10, 2009

Related U.S. Application Data

(63) Continuation of application No. 10/473,998, filed as application No. PCT/EP02/03132 on Mar. 20, 2002, now abandoned.

(30) Foreign Application Priority Data

Apr. 5, 2001  (EP) .................................. 01108607

(51) Int. Cl.
*A61F 2/44* (2006.01)
(52) U.S. Cl. ................................. 623/17.16
(58) Field of Classification Search ..... 623/17.11–17.16
See application file for complete search history.

(56) References Cited

U.S. PATENT DOCUMENTS

| | | | |
|---|---|---|---|
| 5,507,816 A * | 4/1996 | Bullivant | 623/17.15 |
| 5,556,431 A * | 9/1996 | Buttner-Janz | 623/17.15 |
| 6,368,350 B1 | 4/2002 | Erickson et al. | |
| 2004/0153157 A1 | 8/2004 | Keller | |

FOREIGN PATENT DOCUMENTS

| | | |
|---|---|---|
| EP | 0 298 233 | 1/1989 |
| EP | 0 333 990 | 9/1989 |
| EP | 0 560 140 | 9/1993 |
| EP | 0955021 | 11/1999 |
| WO | WO-0053127 | 9/2000 |

OTHER PUBLICATIONS

Board of Patent Appeals and Intereferences decision dated Sep. 7, 2007 in U.S. Appl. No. 10/473,998.
European Search Report in EP01108607.1 dated Nov. 21, 2001 (3 pages).

* cited by examiner

*Primary Examiner* — Kevin T Truong
*Assistant Examiner* — Michael Araj
(74) *Attorney, Agent, or Firm* — Nutter McClennen & Fish LLP

(57) ABSTRACT

System of intervertebral disc prostheses which includes standard prostheses and corrective prostheses. The corrective prostheses serve to compensate for a ventro-dorsal offset. They are characterized in that, on one of their cover plates, the surface via which it cooperates in a matching manner with the prosthesis core is offset ventrodorsally relative to the contact surface by comparison with the standard prostheses.

12 Claims, 2 Drawing Sheets

SYSTEM FOR INTERVERTEBRAL DISK PROSTHESES

CROSS-REFERENCE TO RELATED APPLICATIONS

This application is a continuation of U.S. patent application Ser. No. 10/473,998, filed Apr. 2, 2004, the entirety of which is incorporated herein by reference.

BACKGROUND OF THE INVENTION

It is known to replace damaged intervertebral discs with prostheses which consist of two cover plates, each to be connected to an adjacent vertebral body, and of a prosthesis core, said prosthesis core cooperating with one or both cover plates via complementary spherical surfaces of articulation (EP-B 298 233). The cover plates have contact surfaces by means of which they are connected to the adjacent vertebral bodies. It is desired that the centre of articulation of the prostheses be arranged in such a way that the movements permitted by the prosthesis are as far as possible identical to the natural ones and that forces can be transmitted uniformly between the vertebral bodies and the prosthesis. In known prostheses, this objective is approached by arranging the centre of articulation in a predetermined spatial relationship to the contact surfaces of the cover plates and by providing the cover plates with an edge which bears on the ventral margin of the associated vertebral body and thereby determines the relative position of the cover plate to the vertebral body (EP-B 560 140), or by using an implantation instrument which has a limit stop on the vertebral body (EP-B 333 990). This ensures an at all times identical position of the centre of articulation of the prosthesis in relation to the ventral edge of the vertebral bodies. It is also known (EP-A 955 021), in a system of intervertebral disc prostheses including several categories of different sizes, to provide corrective prostheses which belong on one side to one size category and on the other side to another size category.

SUMMARY OF THE INVENTION

By means of the abovementioned predetermined spatial relationship of the centre of articulation to the contact surfaces of the prostheses, the desired spatial relationship to the vertebral bodies is achieved only if the anatomical conditions correspond to the normal conditions assumed upon construction of the prosthesis. If, however, for example for anatomical reasons, a centre of articulation is by way of exception to have another position, the prosthesis in question or a cover plate of this prosthesis must be implanted so as to deviate from the normal spatial relationship to the vertebral body, which is difficult and risky.

Starting from the prior art last mentioned above, it is therefore an object of the invention to make the implantation of the prosthesis easier and safer for these cases. This is achieved by the features of claim 1 and preferably by the features of the subclaims.

A system of intervertebral disc prostheses is assumed which includes standard prostheses and corrective prostheses. The standard prostheses in each size category are identical to each other. A plurality of size categories are normally available, although this is not absolutely necessary. The prostheses consist of a prosthesis core and of at least one cover plate. The prosthesis core cooperates with at least one cover plate via articulation surfaces. The prosthesis core preferably has two articulation surfaces on opposite sides via which it cooperates with complementary articulation surfaces of two cover plates. However, it is also possible for one of the cover plates to cooperate in a non-articulating manner with the prosthesis core via retaining surfaces. Articulation surfaces and retaining surfaces are combined below and in the claims under the term core-matching surfaces. The cover plates have a contact surface to adjoin a vertebral body. In this connection, the invention provides for the corrective prostheses to have at least one corrective cover plate whose core-matching surface is offset ventrodorsally relative to the contact surface by comparison with the standard prostheses.

In this way, it is ensured that the centre of articulation of a prosthesis relative to the vertebral body on whose side the corrective cover plate is fitted is offset ventrodorsally compared to the standard prostheses. The offset can be in the ventral direction or the dorsal direction depending on the type and direction of insertion of the cover plate. If the contact surfaces of the corrective cover plates are of symmetrical configuration in relation to their mediolateral centre line, they can either be used with the centre offset in the ventral direction or in the dorsal direction. Since the offset in question is predominantly in the dorsal direction, an essential embodiment of the corrective plate according to the invention is distinguished by the fact that the centre of articulation is offset dorsally, provided that the dorsal side can be distinguished on the cover plate.

Cases arise in which the intervertebral disc prosthesis tends to be offset in an undesired manner because of considerable curvature of the spinal column or because of high ventrodorsal forces acting between the vertebrae concerned. This is true in particular of those prostheses in which the prosthesis core cooperates with both cover plates via spherical articulation surfaces. In this type of prosthesis, the cover plates are able to move slightly in translation relative to each other in an angular position of the prosthesis core under relative lateral forces. The use of the invention is particularly advantageous in this type of prosthesis because the corrective plates make it possible to arrange the centre of articulation of one cover plate so that it is displaced relative to the centre of articulation of the other cover plate, as a result of which said offset is compensated.

The diameter of the articulation surfaces can be chosen as large as possible within the limits of the cover plate in order to keep the surface pressure low. In known prostheses, the articulation surface formed on the cover surface has an only slightly smaller ventrodorsal extent than the cover plate. In these cases the offset of the articulation surface relative to the contact surface can take place only under the proviso that a smaller diameter is chosen for the articulation surface. If the radius of curvature of the articulation surface is left unchanged, the depth of the articulation surface provided in the cover plate decreases as the diameter decreases and thus its ability to transmit forces acting laterally (parallel to the plane of the cover plate). This may be acceptable in some cases, so that this embodiment of the invention is not excluded. However, an embodiment is preferred in which the diameter and the radius of curvature of the articulation surface of the corrective cover plate are chosen to complement the articulation surfaces which belong to another, smaller size category. In the smaller size category, not only is the diameter of the articulation surfaces chosen smaller, but also the radius of curvature. The depth of these smaller articulation surfaces is therefore greater than the depth of an articulation surface of the larger size category, in which only the diameter was reduced, but not the radius of curvature.

Choosing an articulation surface (or other core-matching surface) admittedly rules out using the corrective cover plate together with prosthesis parts which belong to the same size category. However, instead of this, prosthesis parts can be used which belong to the smaller size category, on whose basis the articulation surface of the corrective cover plate was chosen. The prosthesis core is preferably in all cases a standard prosthesis core. The second cover plate belonging to the prosthesis is likewise preferably a standard cover plate. However, if a particularly large offset of the two contact surfaces of the prostheses relative to each other is wanted, the second cover plate can also be a corrective cover plate, which is, however, rotated though 180. degree. in relation to the first one so that the offset amounts of both plates are added to each other. It is only if, for some reason, the centre of articulation of the prosthesis is to be displaced ventrally or dorsally in relation to both adjacent vertebrae that corrective cover plates are used in the same orientation on both sides.

In the case of the corrective cover plates, as a result of the offset arrangement of the core-matching surface relative to the contact surface, on one side of the core-matching surface there is a distance between this and the plate edge. If this part of the surface is not needed in order to make available as large a contact surface as possible, the plate can be shortened on this side. The contact surface is then the same width in the mediolateral direction as the standard cover plates of the same size category, but its dimension in the ventrodorsal direction is smaller and can correspond to the smaller size category. This can afford advantages in terms of adjustment in cases where the vertebral bodies are wider in the mediolateral direction and narrower in the ventrodorsal direction.

BRIEF DESCRIPTION OF THE FIGURES

The invention is explained in more detail below with reference to the drawing which depicts advantageous illustrative embodiments and in which.

DESCRIPTION OF THE INVENTION

Figure 1:
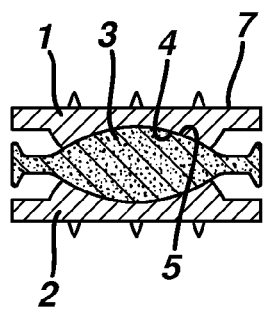
FIG. 1 shows a medial section through a standard prosthesis of a first size category.
Figure 2:
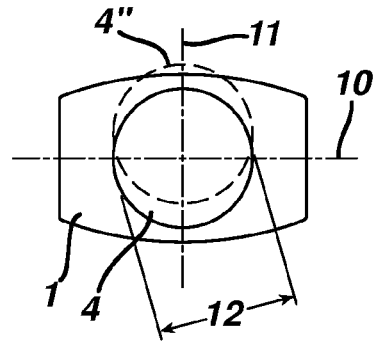
FIG. 2 shows a view of the inside of a cover plate of a standard prosthesis of the first size category.
Figure 3:
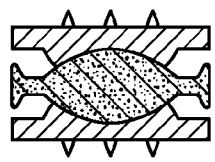
FIG. 3 shows a medial section through a standard prosthesis of a second size category.
Figure 4:
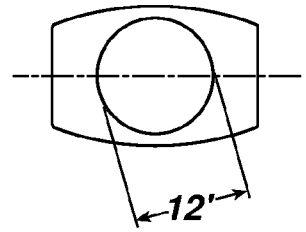
FIG. 4 shows a view of the inside of a cover plate of the standard prosthesis according to FIG. 3.

The standard prostheses according to FIGS. 1 to 4 consist of a lower cover plate 1, an upper cover plate 2 and a prosthesis core 3. The cover plates form spherical, concave articulation surfaces 4, and the prosthesis core 3 forms two identical convex, spherical articulation surfaces 5 which lie opposite each other and which are designed to complement those of the cover plates. All dimensions of the first size category (FIGS. 1 and 2) are greater than those of the second size category (FIGS. 3 and 4). In addition to the two size categories shown, further size categories can be present within the system.

The components of the prosthesis can be made of materials which have proven suitable for endoprostheses, for example metal, ceramic, polyethylene, with the cover plates 1, 2 preferably being made of rigid material (for example metal) and the prosthesis core preferably being made of polyethylene.

The cover plates 1, 2 have a contact surface 7 which is intended for connection to the end face of a vertebral body. It can be equipped with means (not shown) for fixed connection to the bone, for example teeth. It is more extensive in the mediolateral direction, which is indicated by the line 10 in FIG. 2, than it is in the ventrodorsal direction 11. The diameter 12 of the articulation surface 4 in the standard prostheses is as large as is permitted by the dimension of the cover plate in the direction 11. These explanations concerning FIGS. 1 and 2 apply likewise to the second size category according to FIGS. 3 and 4.

As is known, such prostheses are able to transmit from vertebra to vertebra the forces extending in the direction of the spinal column, and to a certain extent also the forces extending transverse to the latter, and at the same time they permit swivel movements. If they are implanted between vertebrae between which strong transverse forces act, or between which a substantial directional change takes place, as is often the case for example between the last lumbar vertebra and the sacrum, a displacement of the cover plates and of the vertebrae may occur. This can be compensated for by using a corrective prosthesis. It is constructed, for example, as is shown in FIG. 5 or FIG. 7.

Figure 5:
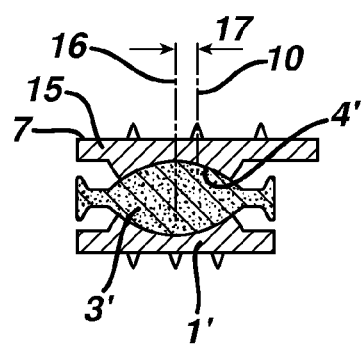
FIG. 5 shows a first embodiment of a corrective prosthesis in medial section.
Figure 6:
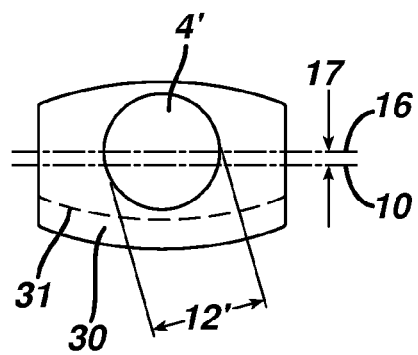
FIG. 6 shows a view of the inside of the associated corrective cover plate.

According to FIG. 5, the corrective prosthesis has an upper cover plate 15 which is designed as a corrective cover plate. The external dimensions of its contact surface 7 and thus the overall surface dimensions are equal to those of the standard cover plate 2 of the first size category. The centre 16 of the articulation surface 4' provided on its inside is displaced dorsally in relation to the centre line 10 by an amount 17. If one were to use the articulation surface 4 of the standard cover plate for this, it would assume the position 4" indicated by the broken line in FIG. 2. As this is partially extending out beyond the edge of the standard prosthesis, the latter would have to be provided at this location with a projection or a widening, or the articulation surface would have to be shortened to correspond to the standard edge contour. Both of these options are within the scope of the invention but are not generally expedient. The embodiment according to FIG. 6 is thus preferred, in which use is made of that articulation surface 4' of the second size category whose diameter 12' is correspondingly smaller and can therefore be accommodated within the edge of the standard format of the corrective cover plate 15. Matching this articulation surface 4', the corrective cover plate 15 is combined with a prosthesis core 3' and a lower cover plate 1' of the second size category, as is indicated in FIG. 5. If, in this corrective prosthesis, the position of the articulation centre line 16 is compared with the position of the contact surface 7 of the corrective cover plate 15, it can be seen that, unlike in the standard prosthesis, these do not coincide but instead are offset in relation to one another by the amount 17.

Figure 7:
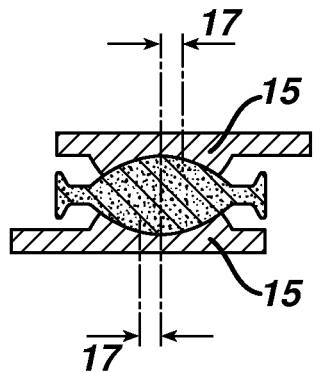
FIG. 7 shows a second embodiment of the corrective prosthesis in medial section.

Instead of being connected to a standard cover plate 1' of the second size category (FIG. 5), a corrective cover plate 15 turned through 180. degree. can also be used as lower cover plate in the corrective prosthesis (FIG. 7). The offset 17 obtained on the lower cover plate is added to the offset 17 on the upper cover plate with the result that the corrective prosthesis according to FIG. 7 provides twice the offset of that according to FIG. 5.

Figure 8:
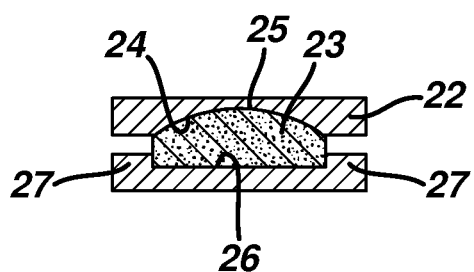
FIGS. 8, 9 show medial sections through standard prostheses of different size categories in a modified embodiment.
Figure 9:
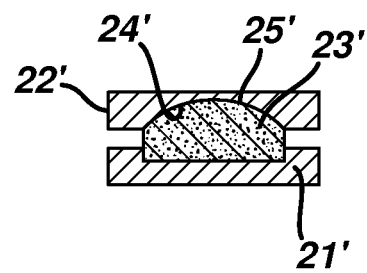

As has been stated, the invention is especially suitable for the prosthesis type shown in FIGS. 1 to 7 in which the prosthesis core 3 has two articulation surfaces 5 opposite each other. However, the invention can also be used in prostheses of the prosthesis type shown in FIGS. 8 to 11. FIGS. 8 and 9 show medial sections through prostheses of different size categories. They consist of a lower cover plate 21, 21', an upper cover plate 22, 22' and a prosthesis core 23, 23'. The upper cover plate 22, 22' and the top of the prosthesis core 23, 23' are identical to those of the illustrative embodiment discussed above. They afford a possibility of articulated movement along the pair of articulation surfaces 24, 25. The underside of the prosthesis core 23 is made flat. The lower cover plate 21, 21' and its core-matching surface 26 with edge 27 is designed solely to hold the prosthesis core 23, 23'.

Figure 10:
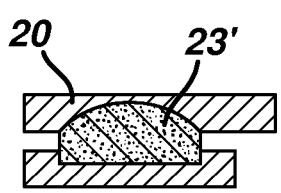
FIGS. 10, 11 show two corrective prostheses for the modified embodiment.

According to FIG. 10, the upper cover plate 20 is designed as a corrective cover plate according to the explanations given for FIGS. 5 and 6. It belongs to the first, larger size category. It is combined with a prosthesis core 23' and a lower cover plate 21' of the second, smaller size category.

Figure 11:
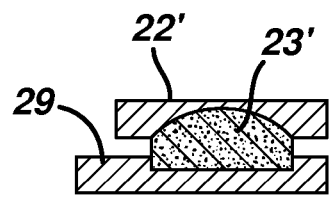

Instead of this, it is also possible according to FIG. 11 to use the lower cover plate 29 as corrective plate. It belongs to the first size category and is combined with a prosthesis core 23' and an upper cover plate 22' of the second size category. As in the examples discussed above, this therefore results in an offset 17 of the centre of articulation relative to the contact surface of the corrective cover plate.

For the sake of simplicity, the offset mentioned in the explanations has been described relative to the contact surface's centre point which, in the standard prostheses, coincides with the centre of articulation of the prosthesis. It goes without saying, however, that the offset can be determined relative to any desired point of the contact surface, in which case its relative position to the articulation centre is to be compared, on the one hand, in a standard cover plate and, on the other hand, upon use of a corrective cover plate.

As can be seen in FIG. 6, the edge strip 30 of the corrective cover plate 15 is not needed for accommodating the articulation surface 4'. If it is also not needed with respect to a desired size of the contact surface 7, it can be dispensed with. The cover plate 15 and its contact surface 7 are then delimited for example according to the broken line 31.

What is claimed is:

1. An intervertebral disc prosthesis comprising:
   a prosthesis core;
   a first cover plate which has a first core-matching surface cooperating with the prosthesis core and a first contact surface intended to adjoin a vertebral body,
   a corrective cover plate which has a second core-matching surface cooperating with the prosthesis core and a second contact surface intended to adjoin a vertebral body, the second core-matching surface being offset ventrodorsally relative to the second contact surface of the corrective cover plate by comparison with the first cover plate which is not offset ventrodorsally when the prosthesis core, the first cover plate, and the corrective cover plate are implanted in a patient.

2. The intervertebral disc prosthesis according to claim 1, characterized in that a dorsal side of the corrective cover plate and the second core-matching surface are offset dorsally relative to the second contact surface.

3. The intervertebral disc prosthesis according to claim 1, characterized in that the diameter of the second core-matching surface of the corrective cover plate is smaller than that of the first cover plate.

4. A system comprising:
   the intervertebral disc prosthesis according to claim 1; and
   a second intervertebral prosthesis comprising
      two corrective cover plates, arranged in opposite directions relative to each other, and a prosthesis core.

5. The intervertebral disc prosthesis according to claim 1, characterized in that the core-matching surfaces are spherical articulation surfaces.

6. An intervertebral disc prosthesis comprising:
   a prosthesis core;
   a first cover plate having a first core-matching surface and a first contact surface, the first core-matching surface being in direct contact with the prosthesis core, and the first contact surface being configured to connect to a first vertebral bone; and
   a second cover plate having a second core-matching surface and a second contact surface, the second core-matching surface being in direct contact with the prosthesis core, and the second contact surface being configured to connect to a second vertebral bone;
   wherein a longitudinal central axis of the second contact surface is laterally offset from a longitudinal central axis of the second core-matching surface in a first direction, and a longitudinal central axis of the first contact surface is laterally offset from the longitudinal central axis of the first core-matching surface in a second direction that is opposite to the first direction when the first contact surface is connected to the first vertebral bone and the second contact surface is connected to the second vertebral bone.

7. The intervertebral disc prosthesis according to claim 6, wherein the longitudinal central axes of the first and second core-matching surfaces are coaxial.

8. The intervertebral disc prosthesis according to claim 6, wherein the first and second core-matching surfaces are articulating surfaces such that the first and second cover plates can each articulate relative to the prosthesis core, a center of the articulation of the second cover plate being the longitudinal central axis of the second core-matching surface.

9. The intervertebral disc prosthesis according to claim 8, characterized in that a center of the articulation of the first cover plate is the longitudinal central axis of the first core-matching surface.

10. The intervertebral disc prosthesis according to claim 6, characterized in that the first core-matching surface is a non-articulating surface such that first cover plate cannot articulate relative to the prosthesis core, and the second core-matching surface is an articulating surface such that second cover plate can articulate relative to the prosthesis core, a center of the articulation of the second cover plate being the longitudinal central axis of the second core-matching surface.

11. The intervertebral disc prosthesis according to claim 6, characterized in that the first core-matching surface is an articulating surface such that first cover plate can articulate relative to the prosthesis core, and the second core-matching surface is a non-articulating surface such that second cover plate cannot articulate relative to the prosthesis core.

12. The intervertebral disc prosthesis according to claim 6, characterized in that a longitudinal central axis of the second contact surface is laterally offset from a longitudinal central axis of the first core-matching surface and from a longitudinal central axis of the second core-matching surface.

* * * * *